United States Patent [19]

Bessler et al.

[11] Patent Number: 4,721,706
[45] Date of Patent: Jan. 26, 1988

[54] CONTROLLING GRAIN INSECTS WITH PHOSPHATIDES

[75] Inventors: Terry R. Bessler; Nathan Kessler; Frank T. Orthoefer, all of Decatur, Ill.

[73] Assignee: A.E. Staley Manufacturing Company, Decatur, Ill.

[21] Appl. No.: 470,828

[22] Filed: Feb. 28, 1983

[51] Int. Cl.$^4$ ............................................. A01N 57/26
[52] U.S. Cl. ..................................................... 514/78
[58] Field of Search .......................... 424/199; 514/78

[56] References Cited

U.S. PATENT DOCUMENTS

| | | | |
|---|---|---|---|
| 1,938,864 | 12/1933 | Rewald | 424/199 |
| 2,006,227 | 6/1935 | Bousquet | 424/199 |
| 2,585,026 | 2/1952 | Moen et al. | 99/80 |
| 3,682,653 | 8/1972 | Mommer | 426/309 |
| 4,208,433 | 6/1980 | Barham, Jr. et al. | 426/69 |
| 4,237,113 | 12/1980 | Cardarelli | 424/78 |

FOREIGN PATENT DOCUMENTS 0068297  1/1983  European Pat. Off. .

OTHER PUBLICATIONS

Soybeans; American Soybean Association; Aug. 30, 1982; Hamon.
Decatur Herald and Review; "Potential Seems Limitless"; Jan. 23, 1983.
Groundnut Oil Treatment for the Control of Callosobruchus Maculatus (F.) During Cowpea Storage—S. R. Singh et al.—Jr. Stored Prod. Res., vol. 14, pp. 77-80, 1978.
Use of Vegetable Oils to Protect Stored Beans from Bruchid Attack, A. V. Schoonhoven, J. Econ. Entomol., vol. 71, pp. 254-256, 1978.
Protection of Stored Wheat from the Granary Weevil by Vegetable Oils, Y. T. Qi et al., J. Econ. Entol., vol. 74, No. 5, pp. 502-505, 1980.
Control of Grain Dust with a Water Spray—F. S. Lai et al., Cereal Foods World, vol. 27, No. 3, pp. 105-107, 1982.
Reducing Grain Dust with Oil Additives—F. S. Lai et al., Transactions of the ASAE, vol. 24, No. 6, pp. 1626-1631, 1981.
Effectiveness of Vegetable Oil Fractions in Controlling the Mexican Bean Weevil on Stored Beans, J. Hill and A. V. Schoonhoven, Jr. of Econ. Entomology, 74, Aug. 1981, p. 478.

*Primary Examiner*—Albert T. Meyers
*Assistant Examiner*—Joseph A. Lipovsky
*Attorney, Agent, or Firm*—Michael F. Campbell; James B. Guffey; J. Daniel Wood

[57] ABSTRACT

Insect infestation of grain is controlled by contacting the grain, or a locus separating the grain from an insect population, with an insecticidally effective amount of a liquid comprising a concentration of phosphatides greater than that found in crude vegetable oils. The dust associated with the grain is controlled as well when the grain is contacted with the liquid.

3 Claims, No Drawings

CONTROLLING GRAIN INSECTS WITH PHOSPHATIDES

FIELD OF THE INVENTION

This invention relates to the control of grain insects with phosphatide-containing liquids. More particularly, one embodiment of this invention relates to a process in which grain, or a locus separating the grain from an insect population, is contacted with a phosphatide-containing liquid to control insect infestion of the grain. When the grain is contacted with the liquid, the dust associated with the grain is controlled as well. Another embodiment of this invention relates to a liquid, phosphatide-containing insecticide and grain-dust suppressant composition.

BACKGROUND OF THE INVENTION

1. Insect Infestation

It has been estimated that about ten percent of the world's grain production is lost during storage because of insect infestation. Not only do the insects consume the grain, but they also generate dust and contaminate the grain with insect fragments, feces, webbing, metabolic products, and a variety of microflora. Because of the size of the losses, there has been a tremendous amount of research on the control of insects. While methods of control studied have included improved sanitation and physical separation methods, probably the most common method of control is the application of an insect control agent on or near the grain. Insect control agents act in many different ways; for example, some kill the insect upon physical contact or ingestion, some disrupt the reproductive cycle, and some merely repel the insects. Insect control agents include various biological agents, such as pheromones, and chemical agents, such as insecticides. At this time, the chemical agents are more frequently used than the biological agents.

Chemical insecticides are widely recognized as effective at controlling insects. Such insecticides can be applied as dusts, wettable powders, aerosols, solutions, and emulsions. Although effective, chemical insecticides suffer serious drawbacks because of toxic residues they leave on the grain and the serious dangers they pose to workers handling them and/or the treated grain. Accordingly, the use of chemical insecticides on food materials is strictly regulated. Another drawback is that the chemical insecticides are generally quite expensive and, since many of these insecticides and/or their carriers are derived from petroleum-based feedstocks, their costs have rapidly increased over the past decade. Last but not least of the drawbacks is the phenomenon of genetic resistance which decreases the effectivess of a given insecticide over time.

Therefore, it is not surprising that considerable attention has been focused on the use of substances which control insects when applied to the grain and which are inexpensive, non-toxic, and less prone to the effects of genetic resistance. One such substance is white mineral oil, also called petrolatum, which is a petroleum fraction boiling in the range of about 330° to 390° C. and having a specific gravity at 25° C. of about 0.82 to 0.90. Although white mineral oil is believed to be non-toxic, it is not digestible and therefore adds no nutritional value to the treated grain. And, since it is derived from petroleum, the cost of white mineral oil has increased substantially over the past decade. Another substance which is reported to be effective at controlling insects is vegetable oil. Although vegetable oil has been used since ancient times to protect grain from insect infestation, this use has become the subject of renewed interest. For example, S. R. Singh et al. have reported that cowpea seeds are protected against infestation by the cowpea weevil, *Callosobruchus Maculatus* (F), when treated with groundnut oil at 5 ml/kg or with castor, coconut, or palm kernel oils at 8 ml/kg. S. R. Singh et al., "Groundnut Oil Treatment For The Control of *Callosobruchus Maculatus* (F) During Cowpea Storage", *J. Stored Prod. Res.* (Vol. 14, pp. 77–80, 1978). This study indicated that the method of control was primarily by progeny mortality rather than reduced oviposition (egg-laying) or adult mortality. It was theorized that the action of the oil within the egg may be due to both chemical toxicity and the physical properties of the oil.

In another study, A. V. Schoonhoven tested a number of different vegetable oils for their efficacy in protecting bean seeds, *Phaseolus vulganis* (L.) from attack by the bruchid, *Zabrotes subfasciatus*. A. V. Schoonhoven, "Use of Vegetable Oils to Protect Stored Beans from Bruchid Attack", *J. Econ. Entomol.* (Vol. 71, pp. 254–256, 1978). The oils tested included African palm, crude cottonseed, purified cottonseed, maize, crude soybean, purified soybean, crude coconut palm, and purified coconut palm. Schoonhoven noted that progeny emergence was reduced significantly by the addition of only 1 ml oil/kg of beans and that the addition of 5 ml oil/kg of beans caused 100% adult mortality two days after infestation and completely eliminated oviposition. Schoonhoven also stated that crude oils provided significantly better protection than purified oils and that the level of control of different oils varied significantly. A subsequent article co-authored by Schoonhoven reported that the triglyceride fraction of vegetable oils was the active component in insect control. J. Hill and A. V. Schoonhoven, "Effectiveness of Vegetable Oil Fractions in Controlling the Mexican Bean Weevil on Stored Beans", *J. Econ. Entomol.* (Vol. 74, pp. 478–479, 1981).

Another report concerns the effect of vegetable oils on protecting wheat from infestation by the granary weevil, *Sitophilus granarius* (L). Y. T. Qi and W. E. Burkholer, "Protection of Stored Wheat From the Granary Weevil by Vegetable Oils", *J. Econ. Entol.* (Vol. 74, No. 5, pp. 502–505, 1980). The vegetable oils tested were soybean, maize, peanut, and cottonseed oils. The authors do not state whether the oils were crude or refined. In testing the effect of oil-treated wheat seeds on progeny emergence, Qi and Burkholder noted that treatment at a 1 ml/kg dosage had little effect, but that treatment at a 5 ml/kg dosage significantly reduced progeny emergence for all the oils tested. Similarly, Qi and Burkholder noted that the 5 ml/kg dosage had little effect on mortality of adult weevils, but that significant mortality was produced at the 10 ml/kg level. Soybean oil was said to produce the highest degree of mortality, followed in order by maize, peanut, and cottonseed oils.

As the above reports indicate, the application of vegetable oils in sufficient amounts is believed to control insect infestation. It is also believed that the action of vegetable oils on insects is less prone to the effects of genetic resistance. And, of course, it is well known that vegetable oils are readily available, relatively inexpensive, and non-toxic. The major drawback to the use of vegetable oils is that they are, to a greater or lesser degree, prone to hydrolytic and oxidative rancidity. Therefore, the use of vegetable oil on grain can result in the grain developing an unpleasant odor and/or taste over time. Accordingly, a need still exists for a substance which controls insects and possesses the many other advantages of the vegetable oils, but is less prone to rancidity. Ideally, the substance would also be even more effective at controlling insects so that it could be applied in smaller amounts.

While there is nothing to suggest that phosphatides are effective at controlling insects, the use of lecithin, which contains a high concentration of phosphatides, in insecticide formulations is known. For example, in 40 C.F.R. Section 180.1001 (1982), the use of lecithin meeting Food Chemicals Codex specification as an emulsifier in pesticide formulations is exempted from the requirement of a tolerance. Cardarelli, U.S. Pat. No. 4,237,113, also discloses the use of lecithin as a component in an insecticide formulation. Cardarelli teaches that a slow release insecticide is prepared by mixing together a polyolefin, a halogenated organotin, and an agent which induces and enhances porosity within the polyolefin, and then coalescing the mixture by heating and before partitioning for use. Cardarelli states that the porosity-inducing agent can be insert, but it is preferable to employ an agent which is also an attractant for various insects. The preferred attractant-porosigen agents are soy oil and lecithin.

2. Grain Dust

It is well known that grain dust is an irritant when inhaled, a source of grain loss, a problem to machinery, and a nuisance from a cleanliness standpoint. However, the greatest problem with grain dust is that it is an oxidizable material which, under certain conditions, can ignite and burn. The combustion of the dust is accompanied by an increase in pressure resulting from the conversion of solid reactants to gaseous products. The increase in pressure can occur so quickly that equalization does not occur, resulting in the production of a shock wave. This shock wave can, in turn, produce a violent explosion. Grain dust explosions at grain handling locations have been recorded for hundreds of years. During the two months of December, 1977, and January, 1978 alone, there were seven grain dust explosions in the United States of America resulting in the loss of 62 lives, 55 injuries, and a direct property loss of millions of dollars. It is considered likely that the Occupational Safety and Health Administration will soon, for the first time, prepare grain elevator safety standards limiting accumulations of grain dust.

Mixtures of grain dust and oxygen do not spontaneously ignite; an ignition source of sufficient temperature and energy must be present. However, such sources are often present in grain handling facilites. For example, studies have indicated that probable ignition sources in past explosions include welding, cutting, electrical failures, static electricity, friction sparks, etc. It is also well documented that the ignition and combustion of grain dust is affected by a number of factors, for example, density of the dust; particle size, chemical composition and moisture content of the dust particles; and chemical composition and moisture content of the gas.

There are many precautions taken to reduce the possibility and risks of a grain dust explosion. These are principally mechanical: to reduce sources of ignition and to reduce dust concentration with precipitators, filters and the like. All entail high capital costs and energy expenditures.

A different approach to reducing dust levels is to treat the grain with a dust suppressant. The ideal dust suppressant would have no deleterious effect on the grain and would remain effective at suppressing grain dust for long periods of time so that only one application would be necessary. One grain dust suppressant which has been used with some success is water. See, for example, F. S. Lai et al., "Control of Grain Dust With A Water Spray", *Cereal Foods World* (Vol. 27, No. 3, pp. 105-107, 1982). While water appears to be reasonably effective and is, of course, inexpensive, it is not the ideal suppressant. First of all, water evaporates and may have to be reapplied at each point the grain is handled. Secondly, the addition of water to grain increases the risk of fungus and mold formation and other decay.

Another study has indicated that soybean oil and mineral oil are both effective at suppressing grain dust. F. S. Lai et al., "Reducing Grain Dust With Oil Additives", *Transactions of the ASAE* (Vol. 24, No. 6, pp. 1626-1631, 1981). The researchers found that the addition of 0.04 weight percent soybean oil to Number 1 yellow dent corn reduced its dustiness to 5.4 percent of the control. Because conventionally refined soybean oil is subject to hydrolytic and oxidative rancidity, the researchers used a specially refined soybean oil having an AOM stability of 350 hours to a 100 peroxide value. The addition of mineral oil to the corn caused an even greater reduction in dustiness. The researchers further discovered that the duration of dust suppression was longer for mineral oil than for soybean oil. See also Moen, U.S. Pat. No. 2,585,026 which discloses the use of mineral oil-water emulsions for controlling grain dust.

Barham, Jr., U.S. Pat. No. 4,208,433, discloses the use of vegetable and mineral oils to reduce grain dust. Barham suggests that when the ratio of dust to oil is properly balanced, a synergistic effect results and the oil and the dust are completely incorporated into the grain. Barham states, at col. 7, lines 34-35, that the ratio of dust to oil is usually from 1:1 to 6:1, with 4.5:1 being a common ratio. At col. 20, lines 35-39, Barham states, in effect, that wheat often contains about 0.06 to 0.2 percent dust based on grain weight. Accordingly, to achieve the synergistic effect, it would be expected that the oil be present in an amount of about 0.01 to 0.2 weight percent of the grain. Barham states that "oils, fats, and greases of all sources are applicable" and that the choice for commercial application "will center around the relative costs and intended usage."

Notwithstanding the above-described teaching, a need still exists for a dust suppressant which is inexpensive, more stable, more effective, and which can impart other favorable properties to the grain.

SUMMARY OF THE INVENTION

The general object of one embodiment of this invention is to provide an improved process for controlling insect infestation of grain. A more particular object is to provide such a process which also controls the dust associated with the grain.

We have discovered a new and improved process for controlling insect infestation of grain. The process comprises contacting the grain, or a locus separating the grain from an insect population, with an insecticidally effective amount of a liquid comprising a concentration of phosphatides greater than that found in crude vegetable oils whereby, when the grain is contacted with the liquid, the dust associated with the grain is controlled. This process offers two significant advantages over the use of crude or refined vegetable oils for the control of grain insects and dust. First of all, this process is much more effective at controlling both insects and dust. Secondly, this process is not deleterious to the grain because the phosphatides do not develop rancidity.

The general object of another embodiment of this invention is to provide an improved liquid insecticide and grain dust suppressant composition. A more particular object is to provide a composition in which a recognized insect control agent is present in a carrier liquid which is itself an insecticide and, in addition, a dust suppressant.

We have discovered a new and improved liquid insecticide and grain dust suppressant composition. The composition comprises a recognized insect control agent and a concentration of phosphatides greater than that found in crude vegetable oils. This composition offers the advantage of providing the insect control agent in the desired dosage to the grain while at the same time the carrier liquid augments the control of insects and also controls grain dust.

DETAILED DESCRIPTION OF THE INVENTION

1. Phosphatides

Phosphatides (also called phospholipids) are a group of lipid compounds which yield, on hydrolysis, phosphoric acid, an alcohol, a fatty acid, and a nitrogenous base. Phosphatides are widely distributed in nature and include such compounds as phosphatidyl choline (also called chemical lecithin), phosphatidyl ethanolamine (also called cephalin), and the inositol phosphatides. For commercial purposes, phosphatides are derived from a number of animal and vegetable sources, with the largest source being crude soybean oil. Phosphatides are generally solid compounds which do not melt, but instead degrade and burn when heated to a temperature above about 140° F. Since they contain both hydrophilic and lipophilic segments, the phosphatides are used as emulsifying, dispersing, and wetting agents. In addition, the phosphatides are very resistant to hydrolytic and oxidative rancidity and have been used commercially as anti-oxidants. Phosphatides are also believed to possess significant nutritional benefits. For example, it has been suggested that the ingestion of phosphatides may aid digestion and reduce cholesterol.

Since phosphatides are solids, they must be dissolved and/or dispersed in carrier liquids for use in this invention. The concentration of phosphatides in the liquid need not affect the amount of phosphatides applied to the grain because the total amount of liquid used can be varied according to concentration. However, to ensure efficacy in controlling insects and dust and to ensure ease of handling, the concentration of phosphatides should be such that the liquid has a viscosity at 77° F. of about 0.05 to 100 poise. Within this range it is recognized that, as the concentration of phosphatides increases, efficacy will increase but ease of handling will decrease. The liquids used in this invention contain a concentration of phosphatides greater than that found in crude vegetable oils, which varies from a maximum of about 3.0 weight percent, based on total weight of the oil, in some crude soybean oils to about 0.1 weight percent in crude rapeseed oil. In general, the concentration of phosphatides in the liquid used in this invention should be about 10 to 90 weight percent. The concentration is preferably about 35 to 75 weight percent.

The carrier liquid employed to dissolve and/or disperse the phosphatides should be one which is suitable for use on a food material and which produces a solution/dispersion within the desired viscosity range. Vegetable oils, both crude and refined, are preferred as carrier liquids because such combinations are readily available and because it has been shown that vegetable oils possess some insecticidal and dust suppressant properties themselves.

One preferred source of phosphatides is commercial soybean lecithin (also called natural lecithin or whole lecithin) which is a by-product from the refining of soybean oil and is an article of commerce. Crude soybean oil from a solvent extraction process generally contains about 1.0 to 3.0 weight percent phosphatides. When the crude oil is refined, the first step normally is to remove the phosphatides. This step, often called "degumming", is accomplished by first adding water to the crude oil. The water hydrates the phosphatides and makes them less soluble in the oil. The denser phosphatides and water are then separated from the less dense oil in centrifuges. The removal of the water from the dense phase results in a product having approximately equal amounts of phosphatidyl choline, phosphatidyl ethanolamine, and the inositol phosphatides. Partially refined soybean oil is commonly added back to produce a liquid product which is flowable at room temperature (sometimes called "fluid lecithin"). Commercial fluid soybean lecithin contains about 50 to 65 weight percent phosphatides and a small amount (less than about 5 weight percent) of various carbohydrates, mineral salts, protein materials, free fatty acids, sterols, and water is normally present. The remainder of commercial soybean lecithin is soybean oil.

Another commercial source of phosphatides is the class of products resulting from the modification of soybean lecithin to improve its hydrophilic properties. Various approaches have been taken to effect the modification. For example, one approach has been to chemically or enzymatically modify ordinary soybean lecithin. A second approach has been to remove certain components from the lecithin and a third approach has been to add certain components to the lecithin. A preferred source of phosphatides is the homogeneous blend of unmodified soybean lecithin and at least one nonionic emulsifier selected from the group consisting of polyoxyalkylene monoglyceride, polyoxyalkylene diglycerides, and the polyoxyethylene derivatives of partial fatty acid esters and hexitol anhydride. This blend is disclosed in Orthoefer, U.S. Pat. No. 4,200,551.

2. Insecticidally Effective Amount

The phosphatide-containing liquids used in the invention are applied to the grain in an amount sufficient to control insect infestation therein. In general, the minimal amount needed for insecticidal effectiveness is about 0.01 weight percent phosphatides. As used here, the term "weight percent phosphatides" refers to the parts by weight of phosphatides per 100 parts by weight of dry grain. When applied in an amount effective to control insects, the phosphatide-containing liquids are, surprisingly, also effective at controlling grain dust. As suggested above, this minimum amount is affected somewhat by the choice of carrier liquid. If the carrier liquid is one which possesses some dust suppressant and insecticidal properties of its own, the amount of phosphatides needed may be reduced.

There is no upper limit on the amount of phosphatides which can be applied to the grain since the properties of dust and insect control increase with the amount used and since there is no limit on the amount of phosphatides which can be ingested with the grain. However, it is believed that at some point the phosphatides on the grain would begin to interfere with subsequent handling and/or processing. As a practical matter, it is unlikely that the phosphatides would be applied in an amount greater than about 1.0 weight percent because the marginal increases in effectiveness above that amount become outweighed by the additional cost of the phosphatides. Therefore, in general, the amount of the liquid to apply is one which deposits about 0.01 to 1.0 weight percent phosphatides on the grain desired to be treated. Preferably, the liquid deposits about 0.05 to 0.5 weight percent phosphatides on the grain.

3. Method of Contacting

The phosphatide-containing liquids can be employed in a number of different ways to control insect infestation of grain. First of all, the liquids can be applied to a locus separating the grain from an insect population, for example, the exterior surfaces of a grain bin. However, since the liquid does not come into contact with the grain, there is no effect on dust suppression. Secondly, the liquids can be added directly to the grain or they can be added to a surface which will later come into contact with the grain. When the grain is contacted with the liquid, whether directly or indirectly, the dust associated with the grain is controlled.

The contacting can be performed at any time, from harvest to consumption, when the control of insect infestation and/or dust is desired. Because one application is effective for long periods of time, contacting of the grain shortly after harvest maximizes the benefits. An especially advantageous time for contacting occurs when the grain is brought from the field and placed into storage at an elevator. This is generally a time when grain dust first becomes a problem and when the grain may be exposed to insect infestation over an extended period of time. In addition, equipment is frequently available at elevators to apply such liquids.

It is desirable that the contacting deposit the phosphatides on the grain in a uniform manner. If the phosphatide-containing liquid is poured onto the grain, subsequent mixing is generally required to produce a uniform distribution. A preferred method of contacting is to spray the liquid onto the grain or onto the surface to be contacted, because a uniform distribution can be obtained without mixing. Depending on the viscosity of the liquid employed, it may be desirable to heat the liquid to facilitate handling.

From an insect-and dust-control viewpoint, it is desirable to treat all the grain subject to insect infestation and dust problems. This treatment can advantageously be performed by spraying the grain as it is conveyed from one location to another. However, to greatly reduce the costs of application and to provide some dust control and protection from insect infestation, a different method of application can be used. With this method, the phosphatide-containing liquid is first sprayed onto the interior surfaces of the empty vessel into which the grain is to be placed. The grain is then added without application of the liquid. The upper surface of the filled grain is then sprayed. This final spray settles the dust previously generated and helps suppress new dust formation. Although the interior grain is not treated and will be subject to further insect infestation if the grain already contained insects, the repellency of the liquid present on the exterior grain will serve to prevent new insect infestation from the outside. Surprisingly, the phosphatide present on the exposed grain repels insects and prevents infestation by this route.

4. Types of Grains

This invention may be practiced on virtually any grain or other seed material which is susceptible to insect infestation and dust formation. The term "grain" is used here to include both the raw grain as harvested by the farmer and the products therefrom. In the United States of America, the more common grains include corn (also known as maize), soybeans, wheat, oats, rye, barley, grain sorghums, flax, and rice.

5. Insects Controlled

When present in an effective amount, the phosphatide-containing liquids of this invention function as insecticides by producing adult mortality, by reducing oviposition, by reducing progeny emergence, and by repelling adults. The liquids are especially suitable for controlling the granary weevil, *Sitophilus granarius* (L.), which is a major pest to stored grains in the United States of America. Other insects which are controlled by this invention and which are common in the United States of America include the rice weevil, *Sitophilus oryzae* (L.); the maize weevil, *Sitophilus zeamais* Motschulsky; the Angoumois grain moth, *Sitotraga cerealella* (Olivier); and the lesser grain borer, *Rhyzopertha dominica* (F.). Unlike many of the chemical insecticides, the phosphatide-containing liquids of this invention are also effective at controlling members of the order Acarina such as mites and ticks.

6. Recognized Insect Control Agent

The phosphatide-containing liquids used in this invention can be used advantageously as a carrier/diluent/solvent for recognized insect control agents. The term "recognized insect control agent" includes any substance, other than a phosphatide, which is now, or may be in the future, recognized as having an effect on insects which serves to reduce their infestation of grain. Currently recognized insect control agents include both biological compounds, such as hormones, pheromones, sterilants, and chitin synthesis inhibitors; and chemical compounds, such as insecticides and fumigants. The chemical insecticides include the inorganic insecticides, such as the arsenicals and the fluorides; the natural organic insecticides, such as the pyrethroids, the rotenoids, and the nicotinoids; and the synthetic organic insecticides, such as the organochlorines, the organophosphoruses, the carbamates, the dinitrophenols, the organothiocyanates, and the synthetic pyrethroids. Specific examples of common organochlorines include DDT, toxaphene, lindane, chlordane, aldrin, and heptachlor. Examples of common organophosphoruses include methyl parathion, malathion, parathion, and diazinon. Commonly used carbamates include carbaryl, carbofuran, and propuxur. The use of the phosphatide-containing liquid in conjunction with the recognized insect control agents is advantageous because the control agent can be applied to the grain in the desired dosage while at the same time the carrier liquid augments the control of insects and also controls grain dust.

The following examples are illustrative only.

EXAMPLE 1

This example illustrates that commercial soybean lecithin is more effective at producing mortality of the granary weevil, Sitophilus granarius (L.), than various corn and soybean oils.

Insect mortality was studied by coating petri dishes (9 centimeters in diameter) with a given amount of a lecithin or oil sample dissolved in 2 milliliters of acetone. After the acetone had completely evaporated, 20 adult granary weevils (10 males and 10 females) were placed in each dish. The number of dead insects in each dish was then counted periodically. A control was run using no lecithin or oil. Five replicates were used for each dosage.

Sample A was a crude corn oil. The oil was obtained by the wet milling of whole corn, physical separation of the germ from the other components, and then expression and solvent extraction of the oil contained in the germ.

Sample B was a partially refined corn oil. The crude corn oil described above was first treated to remove the free fatty acids by the addition of an alkali solution followed by physical separation of the solid fatty acid derivatives from the oil. The oil was then washed twice with water and dried under a vacuum. The properties of the partially refined corn oil are given in Table I.

TABLE I

| Properties of Partially Refined Corn Oil | |
| --- | --- |
| Property | Value |
| Free fatty acid concentration (wt. %) | 0.03–0.05 |
| Iodine Value | 122–128 |
| Refractive Index (25° C.) | 1.471–1.475 |
| Specific Gravity (60° F.) | 0.922–0.928 |

Sample C was a fully refined corn oil. This oil was produced by subjecting the partially refined corn oil described above to the additional steps of bleaching, winterizing, and deodorizing. The bleaching process is the addition of an absorbent to the oil and subsequent removal by filtration. The winterizing process is the cooling of the oil to about 40° F. and subsequent filtration. To deodorize, the oil is passed through a tower operated at a pressure of less than about 10 millimeters mercury to remove volatile impurities. The properties of the fully refined corn oil are given in Table II.

TABLE II

| Properties of Fully Refined Corn Oil | |
| --- | --- |
| Property | Value |
| Free fatty acid concentration (wt. %) | 0.03–0.05 |
| Iodine Value | 122–128 |
| Refractive Index (25° C.) | 1.470–1.474 |
| Specific Gravity (60° F.) | 0.922–0.928 |

Sample D was a crude soybean oil. This oil was derived by processing soybeans as follows. The beans are first "cleaned" by physically separating the beans from debris, etc. The cleaned beans are then "cracked" by breaking the beans into several pieces. The light weight hulls are then removed and the bean sections are steamed. The bean sections are then rolled into flakes of a thickness of about 0.015 inches. The flakes are then treated with a solvent to extract the oil. The crude oil is then separated from the solvent by evaporation.

Sample E was a partially refined soybean oil produced from crude soybean oil described above by degumming, alkali-refining, water-washing, and vacuum-drying. These steps are similar to those used in producing partially refined corn oil. The properties of the partially refined soybean oil are given in Table III.

TABLE III

| Properties of Partially Refined Soybean Oil | |
| --- | --- |
| Property | Value |
| Free fatty acid concentration (wt. %) | 0.02–0.04 |
| Iodine Value | 128–134 |
| Refractive Index (25° C.) | 1.471–1.475 |
| Specific Gravity (60° F.) | 0.922–0.928 |

Sample F was a fully refined soybean oil. This oil was produced by bleaching and deodorizing partially refined soybean oil described above. The bleaching and deodorizing steps are similar to the steps followed in fully refined corn oil. The properties of the fully refined soybean oil are given in Table IV.

TABLE IV

| Properties of Fully Refined Soybean Oil | |
| --- | --- |
| Property | Value |
| Free fatty acid concentration (wt. %) | 0.02–0.04 |
| Iodine Value | 128–134 |
| Refractive Index (25° C.) | 1.471–1.475 |
| Specific Gravity (60° F.) | 0.922–0.928 |

Sample G was commercial soybean lecithin. The lecithin was produced by taking the dense phase from the oil degumming step, drying it, and adding filtered crude soybean oil thereto. The properties of soybean lecithin are given in Table V.

TABLE V

| Properties of Soybean Lecithin | |
| --- | --- |
| Property | Value |
| Acetone insoluble phosphatide concentration | 63–65 |
| Viscosity at 77° F. (poise) | 45–75 |
| Specific Gravity (60° F.) | 1.04–1.06 |

Sample H was a water-dispersible blend of commercial soybean lecithin and ethoxylated monoglycerides. The properties of this blend are given in Table VI.

TABLE VI

| Properties of Water-Dispersible Soybean Lecithin Blend | |
| --- | --- |
| Property | Value |
| Acetone insoluble phosphatide concentration (wt. %) | 55–57 |
| Viscosity at 77° F. (poise) | 40–70 |
| Specific Gravity (60° F.) | 1.04–1.06 |

The results of the insect mortality experiments with the eight above-described samples are shown below in Table VII.

TABLE VII

| | | Effect of Vegetable Oils and Lecithin on Mortality of the Granary Weevil | |
| --- | --- | --- | --- |
| | | Dead Weevils (%) | |
| Sample | Dosage (microliters) | 3 Days After Treatment | 5 Days After Treatment |
| Control | 0 | 4 | 28 |
| A | 1 | 5 | 69 |
| | 3 | 36 | 84 |
| | 5 | 97 | 100 |
| B | 1 | 2 | 79 |
| | 3 | 17 | 81 |

TABLE VII-continued

Effect of Vegetable Oils and Lecithin on Mortality of the Granary Weevil

| Sample | Dosage (microliters) | Dead Weevils (%) 3 Days After Treatment | Dead Weevils (%) 5 Days After Treatment |
|---|---|---|---|
|  | 5 | 88 | 97 |
| C | 1 | 5 | 55 |
|  | 3 | 50 | 67 |
|  | 5 | 58 | 77 |
| D | 1 | 4 | 50 |
|  | 3 | 12 | 61 |
|  | 5 | 57 | 91 |
| E | 1 | 11 | 69 |
|  | 3 | 51 | 81 |
|  | 5 | 100 | 100 |
| F | 1 | 12 | 87 |
|  | 3 | 22 | 89 |
|  | 5 | 97 | 99 |
| G | 1 | 17 | 78 |
|  | 3 | 57 | 98 |
|  | 5 | 97 | 100 |
| H | 1 | 23 | — |
|  | 3 | 72 | — |
|  | 5 | 98 | — |

The results show that, at a dosage of 1 microliter and after 3 days, the crude corn oil (Sample A) and the crude soybean oil (Sample D) had virtually no effect on weevil mortality since the percentage of percentage of dead weevils remained relatively constant in comparison with the control. In contrast, the lecithin samples (G and H) showed a very significant effect at this dosage and time. While the control showed only a 4 percent mortality, the soybean lecithin sample (G) showed a 17 percent mortality and the water-dispersible soybean lecithin blend showed a 23 percent mortality. The superiority of the lecithin over vegetable oil also is demonstrated at higher dosages.

EXAMPLE 2

This example illustrates that commercial soybean lecithin has an appreciable effect on the mortality and the number of progeny of the granary weevil, *Sitophilus granarius* (L.) when applied on the grain in an amount greater than 1 ml/kg.

Wheat seeds were treated with the soybean lecithin described in Example 1 as Sample G at dose levels of 1, 3, and 5 ml/kg. Since the lecithin has a specific gravity of about 1.05 and a phosphatide concentration of about 64 weight percent, each milliliter of lecithin contains about 0.7 grams phosphatides. Five gallons of seeds were mixed manually with an appropriate aliquot of lecithin in a wide-mouth 5 gallon glass jar. The treated seeds were then infested with 200 adult granary weevils (100 males and 100 females) aged about one month. The adult insects, both live and dead, were removed 7 days later. The number of progeny was counted 65 days after infestation. A control was run using no lecithin on the wheat. Five replicates were used for each dosage.

The results of the concentration experiment is shown below in Table VIII.

TABLE VIII

Effect of Lecithin Concentration on Mortality and Number of Progeny of the Granary Weevil

| Amount of Lecithin (ml/kg) | Amount of Phosphatides (wt. %) | Average Number of Live Progeny | Average Number of Dead Progeny |
|---|---|---|---|
| 0.0 (Control) | 0.0 | 1052 | 0 |
| 1.0 | 0.07 | 1041 | 0 |
| 3.0 | 0.21 | 161 | 13 |
| 5.0 | 0.35 | 50 | 21 |

The results show that the addition of 1.0 milliliter of lecithin per kilogram of wheat had little effect on the number of progeny and no effect on the ratio of live progeny to dead progeny. However, when the dosage was increased to 3.0 ml/kg, the number of progeny decreased to about 16.5 percent (161+13/1052) of the control. The lecithin at this level also caused the mortality of many of the adults which emerged. The increase in dosage to 5.0 ml/kg resulted in an even greater reduction in the number of progeny and on the mortality of the adults.

EXAMPLE 3

This example illustrates that commercial soybean lecithin on grain repels the granary weevil, *Sitophilus granarius* (L.).

The repellency was tested by placing wheat seeds treated with 2.5 milliliters soybean lecithin per kilogram of seeds (about 0.18 weight percent phosphatides) into a glass vessel having a diameter of 9 centimeters and a height of 12 centimeters. A centrally located vertical brass tube having a diameter of 0.8 centimeters was positioned inside the chamber. The upper end of the brass tube was sealed. The lower end of the tube extended through the floor of the glass vessel into an empty, smaller glass chamber which acted as a trap. The portion of the brass tube within the glass vessel was perforated with holes having a diameter of 3 millimeters.

One hundred adult granary weevils were placed into the glass vessel containing the wheat. The size of the holes in the brass tube enables the weevils to crawl through and drop down into the trap. The number of weevils in the trap was counted periodically. A control was run using untreated wheat and the same number of weevils. Four replicates were used for the control and for the experimental. The results of the repellency experiments are shown below in Table IX.

TABLE IX

Repellency Effect of Lecithin on the Granary Weevil

| Time After Infestation (Hours) | Weevils in Trap (%) Untreated Wheat | Weevils in Trap (%) Lecithin-Treated Wheat |
|---|---|---|
| 1 | 4.7 | 15.5 |
| 24 | 5.5 | 45.5 |
| 48 | 10.5 | 59.7 |
| 72 | 16.5 | 68.2 |
| 96 | 18.7 | 69.7 |
| 120 | 22.0 | 75.3 |

The results show that, 24 hours after infestation, almost one-half (45.5%) of the weevils in the lecithin-treated grain had left the grain and landed in the trap whereas only 5.5% of the weevils in the control had done so. It appears that the repellency effect of the lecithin on the grain accounts for the difference.

EXAMPLE 4

This example illustrates that soybean lecithin is an effective grain dust suppressant.

Dust suppression was studied with 120 pound lots of corn, each having a moisture content of about 12 weight percent. Different proportions of commercial soybean lecithin and of silicone oil was applied to the corn with a siphon-type spray nozzle. The lots were then thoroughly mixed to ensure uniformity. The lots were then poured down a fourteen foot section of a four-inch diameter grain spout at a flow rate of about 100 pounds per minute. The bottom of the spout emptied into a 55-gallon drum. A two-inch diameter plastic tube was connected, at one end, to the upper surface of the spout at a point midway between the inlet and outlet. The other end of the plastic tube was connected to an air flow device which withdrew air through a filter at the rate of about 35 cubic feet per minute from the spout. The air flow device was turned on when the first grain was poured into the spout and was turned off 2 minutes later. The weight of the dust collected on the filter was then measured. A control was run without treatment to suppress dust. Two replicates were used for the control and for the experimentals. The results of the dust suppression experiments are shown below in Table X.

TABLE X

Effect of Lecithin and Silicone Oil on Corn Dust Suppression

| Amount of Lecithin (wt. %) | Amount of Phosphatides (wt. %) | Amount of Silicone Oil (wt. %) | Weight of Grain Dust Collected (grams) |
| --- | --- | --- | --- |
| 0.0 | 0.0 | 0.0 | 18.7 |
| 0.0 | 0.0 | 0.01 | 20.7 |
| 0.0 | 0.0 | 0.02 | 15.2 |
| 0.01 | 0.006 | 0.0 | 1.3 |
| 0.02 | 0.013 | 0.0 | 0.6 |

The results show that the addition of 0.01 or 0.02 weight percent silicone oil to the corn had little effect on reducing the amount of dust in the air above the corn. However, the addition of 0.01 and 0.02 weight percent lecithin (0.006 and 0.013 weight percent phosphatides) reduced the dust to, respectively, 7 and 3 percent of the control.

The foregoing is intended to illustrate the invention which is defined by the claims following. Variations may be made in proportions, materials and procedures without departing from the scope of the invention.

We claim:

1. A method of controlling insect infestation of stored grain which comprises applying to a surface of the vessel in which the grain is to be stored a liquid composition containing about 10 to about 90 weight percent phosphatides and having a viscosity at 77° F. of about 0.05 to 100 poise.

2. The method of claim 1 wherein said liquid composition is applied to the exterior surface of said vessel.

3. The method of claim 1 wherein said liquid composition is applied to the interior surface of said vessel prior to placement of said grain therein.

* * * * *